(12) United States Patent
Puchhammer

(10) Patent No.: US 8,257,446 B2
(45) Date of Patent: Sep. 4, 2012

(54) CLUTCH MODULE FOR PROSTHESIS

(75) Inventor: Gregor Puchhammer, Vienna (AT)

(73) Assignee: Otto Bock Healthcare GmbH, Duderstadt (DE)

( * ) Notice: Subject to any disclaimer, the term of this patent is extended or adjusted under 35 U.S.C. 154(b) by 913 days.

(21) Appl. No.: 12/158,812

(22) PCT Filed: Dec. 13, 2006

(86) PCT No.: PCT/DE2006/002226
§ 371 (c)(1),
(2), (4) Date: Jun. 23, 2008

(87) PCT Pub. No.: WO2007/076795
PCT Pub. Date: Jul. 12, 2007

(65) Prior Publication Data
US 2008/0312753 A1    Dec. 18, 2008

(30) Foreign Application Priority Data

Dec. 23, 2005  (DE) .................. 10 2005 062 400
Feb. 14, 2006  (DE) .................. 10 2006 006 966

(51) Int. Cl.
*A61F 2/54* (2006.01)
*A61F 2/68* (2006.01)

(52) U.S. Cl. ........................................... 623/64

(58) Field of Classification Search ............... 623/61–64, 623/57, 21.15; 192/31, 54.1
See application file for complete search history.

(56) References Cited

U.S. PATENT DOCUMENTS

| 3,883,900 A | 5/1975 | Jerard et al. |
| 5,280,981 A | 1/1994 | Schulz |
| 2002/0077708 A1 * | 6/2002 | Iversen et al. ................... 623/64 |

FOREIGN PATENT DOCUMENTS

| DE | 2335974 | 1/1975 |
| DE | 20301116 | 3/2003 |
| JP | 5-26267 | 9/1991 |
| JP | 6248466 | 9/1994 |
| JP | 10-314198 | 2/1998 |

OTHER PUBLICATIONS

International Search Report for PCT/DE2006/002226, 2 pgs., mailed Apr. 24, 2007.

* cited by examiner

*Primary Examiner* — Bruce E Snow
*Assistant Examiner* — Brian Dukert
(74) *Attorney, Agent, or Firm* — Holland & Hart LLP

(57) ABSTRACT

The invention relates to a clutch module for prostheses, in particular for prosthetic grippers, arm prostheses or hand prostheses that comprise a chassis to which at least one finger prosthesis is articulated, the clutch module including a drive element, a driven element and a clutch device, which shifts between two gear stages depending on the torques applied to the driven element.

18 Claims, 3 Drawing Sheets

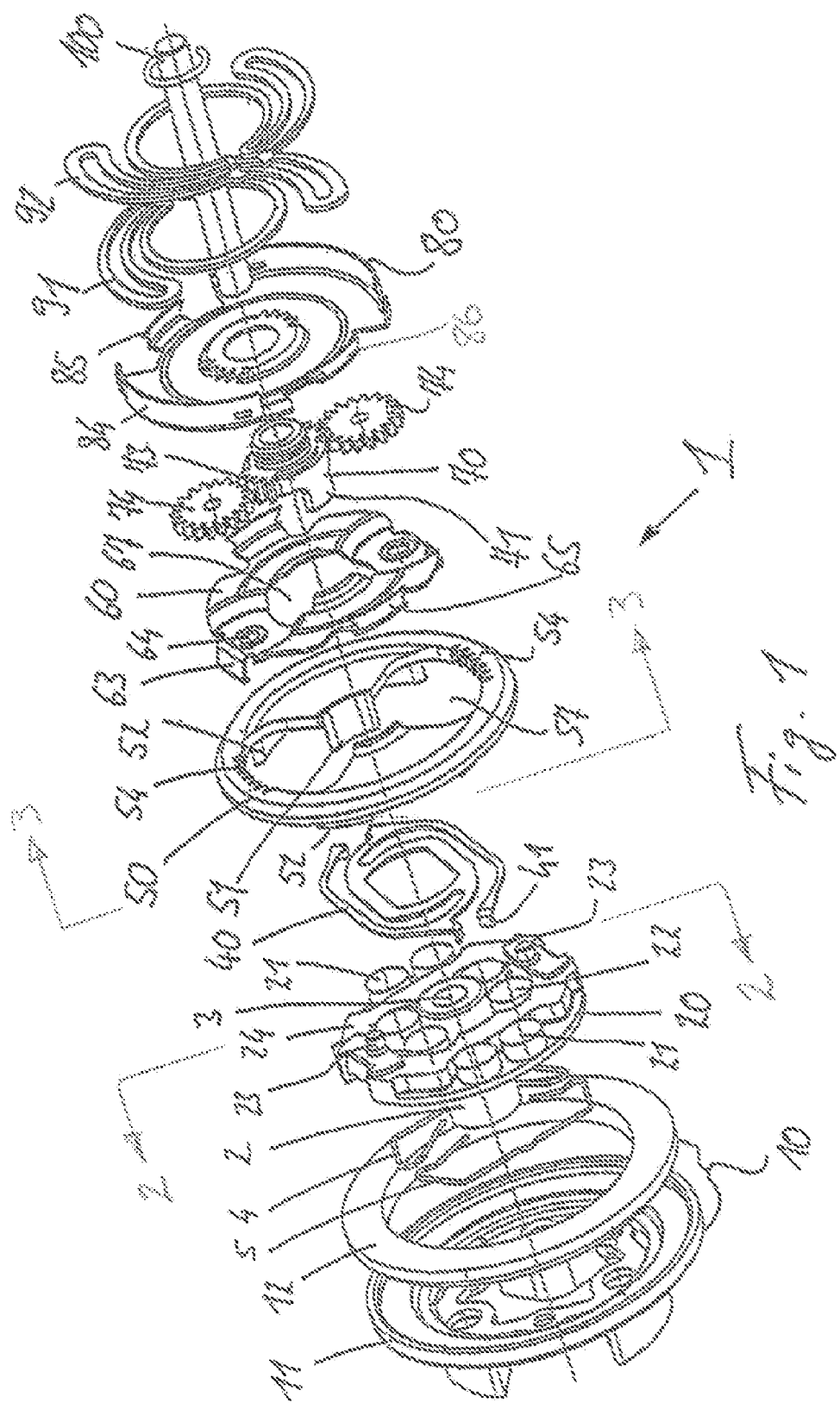

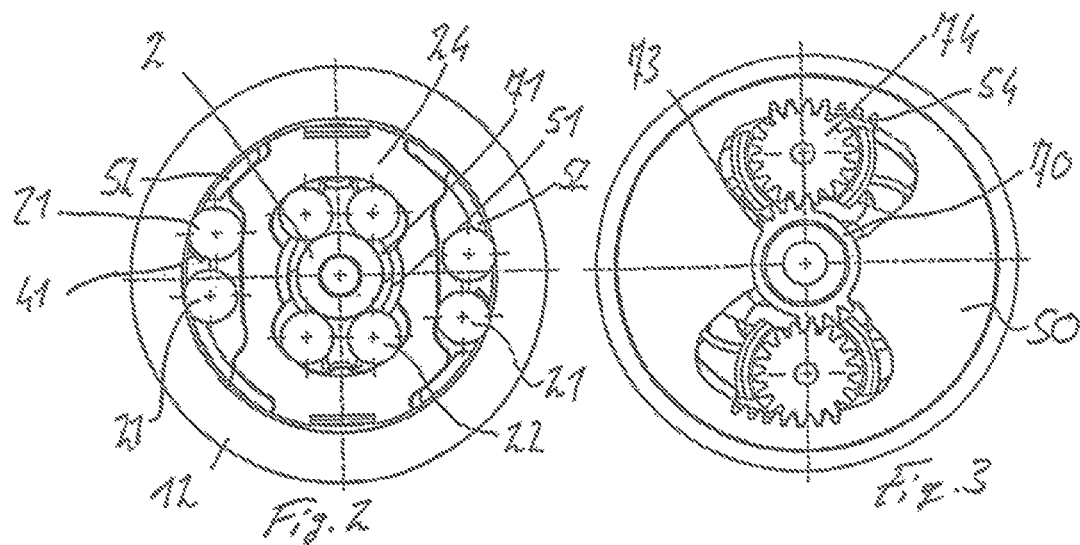
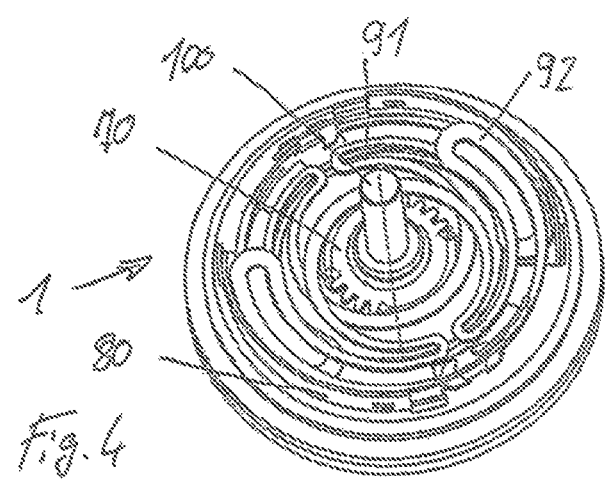

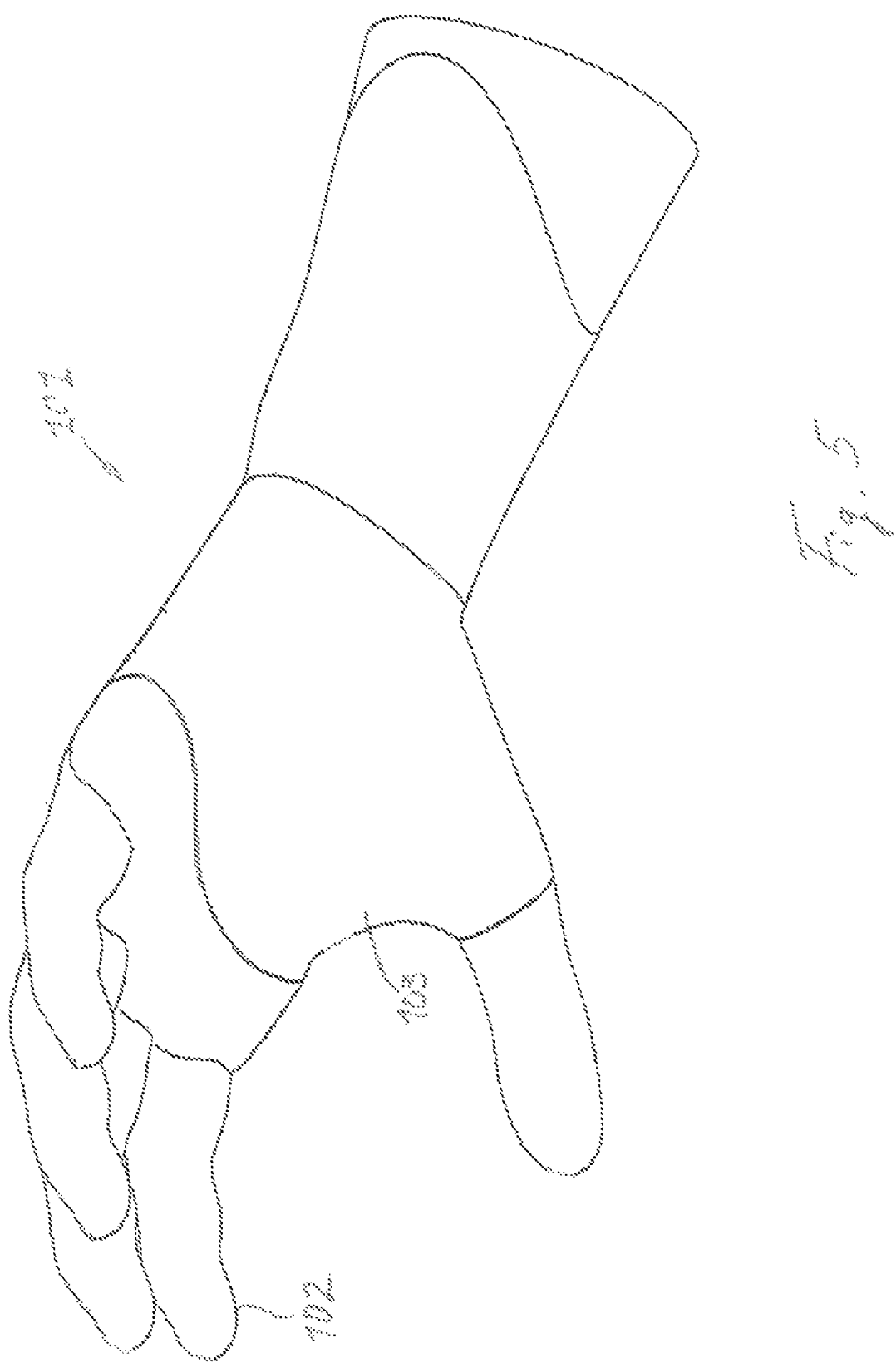

CLUTCH MODULE FOR PROSTHESIS

CROSS-REFERENCE TO RELATED APPLICATIONS

This application is a national phase application, filed pursuant to 35 U.S.C. §371, of PCT/DE2006/002226, filed Dec. 13, 2006 and claims priority to German applications 10 2006 006 966.8 filed Feb. 14, 2006 and 10 2005 062 400.6 filed Dec. 23, 2005, each of which are herein incorporated by reference in their entirety.

FIELD OF THE INVENTION

The invention relates to a clutch module for prostheses, in particular for prosthetic grippers, arm prostheses or hand prostheses that comprise a chassis to which at least one finger prosthesis is articulated, the clutch module including a drive element, a driven element and a clutch device, which shifts between two gear stages depending on the torques applied to the driven element.

BACKGROUND

In prosthetic components such as prosthetic hands, arm prostheses or prosthetic gripping elements, speed-changing mechanisms are provided within the prosthesis to allow not only a high gripping force but also a quick gripping movement to be realized. Such speed-changing mechanisms provide both a high increase in speed to bring gripping elements quickly into contact with the object to be gripped, and a low increase in speed to provide high gripping forces. The shift between the individual gear stages may take place in various ways. Generally, a separate gear mechanism has to be provided for a right prosthetic hand and a left prosthetic hand. Likewise, separate mechanisms are required for gripping and opening the hand. The same also applies in principle to arm prostheses, prosthetic gripping elements or other prostheses that are intended to move into a desired position quickly without using much force, while a slow and forceful movement occurs subsequently.

SUMMARY

An object of the present invention is to provide a gear element with which a fully functional prosthesis or prosthetic gripping device can be configured at lower cost and with lower weight.

One embodiment of the present invention is a clutch module for prostheses such as prosthetic grippers, arm prostheses or hand prostheses that comprising a chassis to which at least one finger prosthesis is articulated, the clutch module having a drive element, a driven element and a clutch device, which shifts between two gear stages depending on the torques applied to the driven element. In this way, an adaptation to the required adjusting or gripping force occurs automatically based on the applied torque. First, a quick adjusting or gripping or opening movement occurs, and if there is an increase in the adjusting or gripping resistance an increased adjusting or gripping force occurs along with a decreased adjusting or gripping speed. When used in a hand prosthesis, the clutch module can also be used for to open the hand. In such a case, a low opening speed with a low rotational speed provides high releasing forces or opening forces. Once the grip has been loosened or the prosthetic fingers have pried an object apart, the adjusting speed increases as the opposing force subsides, so that the gripping elements open more quickly. The shifting is therefore dependent on the torque and independent of the direction of rotation.

In another embodiment the clutch device is in contact with clamping bodies, in particular clamping rollers, which couple the drive element to the driven element in a torque-controlled manner. The clamping bodies make it possible for the clutch module to have a low-wearing and reliable construction and allow the force transmission elements to be coupled to one another independently of the direction of rotation. The independence from the direction of rotation can be accomplished by a symmetrical construction of the force transmission components.

In a further embodiment, the clutch device may have two switching elements, which are mounted such that they are pre-stressed and can turn in relation to each other. The switching elements have switching webs or switching pins, which can be brought into contact with the clamping bodies in a torque-controlled manner. The turning angle of the switching elements in relation to each other may be used to bring clamping bodies, that are respectively to be activated, into contact with the force transmission units, and the clamping bodies make it possible to drive the driven element. In this case, the switching elements may be kept under pre-stress by springs so that the tripping torque or response torque of the clutch module can be set for a low opposing force. The greater the pre-stress of the springs, the greater the opposing force must be to turn the switching elements in relation to each other. This has the effect of increasing the tripping torque, which can be adapted to the individual needs of the wearer of the prosthesis or the user of the prosthetic gripping device. In one embodiment, the springs are exchangeable. Optionally, a different spring rate may be set depending on the adjusting movement, for example, a different spring rate for the opening movement and for the closing movement of a hand prosthesis or prosthetic gripping device, so that different switching times or torques can be set for different opposing forces.

The drive element may be coupled to a gear mechanism, for example a planetary gear mechanism, to be able to realize a speed reduction. In this case, the corresponding speed-reducing gear mechanism has a contact ring, with which the clamping bodies for the transmission of a high torque are in contact.

The clamping bodies or rollers may be arranged on a common driver disk, to minimize installation space. The driver disk has a frame in which clamping bodies are arranged to provide for a high increase in speed. Clamping bodies, which provide for the transmission of a high torque with a low increase in speed, are arranged outside the frame and are in contact with a contact ring of the speed-reducing gear mechanism. By using clamping bodies both for the increase in speed with high torque and low rotational speed and for the increase in speed with low torque and high rotational speed, a sliding transition between the individual gear stages can be realized without a noticeable switching operation within the hand prosthesis.

In one embodiment, gearwheels, a switching disk and a second switching element are mounted on the driver disk. The gearwheels engage and turn a switching ring in relation to the switching disk. This turn is used angle-dependently to perform sequence control of the engagement or disengagement of the clamping bodies or rollers in relation to the respective force transmission components.

BRIEF DESCRIPTION OF THE DRAWINGS

An exemplary embodiment is explained in more detail below on the basis of the accompanying figures, in which:

FIG. 1 shows a clutch module in an exploded representation;

FIG. 2 shows a sectional representation of the clutch module in the force mode;

FIG. 3 shows a sectional representation according to FIG. 2 in another plane;

FIG. 4 shows an assembled clutch module.

FIG. 5 shows an example prosthesis with which the clutch module of FIGS. 1-4 may be used.

DETAILED DESCRIPTION OF THE DRAWINGS

FIG. 1 shows a clutch module 1 in an exploded representation. The clutch module 1 serves for the torque-controlled shifting between a speed mode and a force mode and has a drive shaft 2, on which a driver disk 20 is over-mounted. This driver disk 20 is rotatably mounted in a planet carrier housing 10. Within the planet carrier housing 10 there is a planetary gear mechanism (not shown), a harmonic-drive gear mechanism (not shown) or some other highly speed-reducing gear mechanism. The planet carrier housing 10 has a contact ring 12 having a running surface formed on its inner circumference. For reasons of stability, the contact ring 12 is formed from a solid material such as steel. Alternatively, the running surface of the contact ring 12 may comprise a hardened steel ring. Formed underneath the contact ring 12 is a housing 11, which may be made of plastic to minimize weight. The contact ring 12 and the housing 11 may be fastened to each other or be produced together by a two-component injection-molding process.

The drive shaft 2 is cylindrically formed and has a bore 3, in which a mounting pin 100 may be received to position additional components of the clutch module 1 around it. The drive shaft 2 drives the planetary gear mechanism (not represented), and consequently the planet carrier housing 10 and the contract ring 12, as long as a motor (not represented) is activated. The contact ring 12 therefore constantly runs around the driver disk 20 when the drive is switched on.

Formed on the driver disk 20 is a frame 24 having an inner area, within which a total of four clamping bodies in the form of clamping rollers 22 are arranged. The also frame 24 has outer area, which holds outer clamping bodies in the form of clamping rollers 21. Likewise formed on the frame 24 are pins 23, which serve as spindles for gearwheels 74, the function of which is explained below. Two springs 4, 5 are arranged between the driver disk 20 and the planet carrier housing 10, which keep the clamping rollers 21, 22 in their desired positions. For the same purpose an S-shaped spring 40 is arranged on the side of the driver disk 20 that is facing away from the planet carrier housing 10. The S-shaped spring 40 has downwardly protruding webs 41, which contact the outer clamping rollers 21 and press the latter against switching webs or pins 52 of a switching ring 50. As a result, backlash-free switching of the outer clamping rollers 21 is accomplished.

The switching ring 50 is arranged above the spring disk 40 and has four downwardly protruding, radially outwardly arranged switching webs 52 or switching pins, which serve for the torque-controlled activation of the outer clamping rollers 21. The switching ring 50 also has radially inner switching webs 51 or switching pins, which activate or deactivate the inner clamping rollers 22. Clearances 57 for the gearwheels 74 are formed within the switching ring 50 which engage in a partial internal toothing 54.

A switching disk 60 is arranged on the switching ring 50, which has downwardly protruding contact webs 63, which are positioned, for example pressed or clipped, around corresponding clearances of the driver disk 20 to transmit a torque.

The switching disk 60 has through-holes 64 to receive pins 23. Upwardly bent holding webs 65 into which torsion springs 91, 92 can be hooked are likewise formed on the switching disk 60, and may be formed as a sheet-metal part. A clearance 67 is formed within the switching disk 60, into which a gearwheel element 70 with a partial external toothing 73 and downwardly protruding switching webs 71 or switching pins are rotatably mounted. The switching webs 71 lie radially inward from the switching webs 51 of the switching ring 50 and actuate the diagonally opposing, inner clamping rollers 22.

A cup disk 80 is arranged above the gearwheel element 70 and has a web 84 that runs part of the way around it, in which the torsion springs 91, 92 are mounted. Spring holding webs 85, 86 are likewise formed such that they are bent upward and are arranged radially inwardly from the upwardly bent holding webs 65 on the switching disk 60.

The springs 91, 92 are pre-stressed and engage the spring holding webs 85, 86 of the cup disk 80 and the switching disk 60 to keep them under pre-stress in relation to each other.

The operating mode of the clutch module 1 is explained on the basis of use in a hand prosthesis 101 (see FIG. 5), but the clutch module can also be used in arm prostheses, prosthetic gripping elements or other prostheses with a drive. In the case of hand prostheses or gripping elements, it is beneficial first to permit a speed mode for quick adjustment, for example of the prosthetic fingers 102 relative to a chassis 103 (see FIG. 5), in order to make the contact of the prosthetic fingers or gripping elements with the object to be gripped possible. As soon as first contact has been made, a controlled increase in force is desirable, to allow the gripped object to be held for a period of time. For this purpose, it is necessary to apply higher torques. The increase in torque takes place by way of the planetary gear mechanism (not represented), at the expense of adjusting speed.

In the speed mode, in which a quick opening or closing movement of the gripping elements is desired, the drive shaft 2 is set in rotation by means of a drive (not represented). The inner clamping rollers 22 are in the starting position, bearing slightly against the frame 24 when the drive is not activated due to the springs 4, 5. If the drive is switched on, the respectively diagonally opposed clamping rollers 22 come into contact with the frame in a torque-transmitting manner and clamp, so that torque is transmitted from the drive shaft 2 and the frame 24 onto the driver disk 20. By prestressing springs 4, 5, torque delay is minimized. The torque acts on the switching disk 60 by way of the pins 23 and the cup disk 80 by way of the switching disk 65 60, The cup disk 80, acts as the driven element to pass the torque to corresponding force transmission units.

In this speed mode position, the cup disk 80 and the switching disk 60 are kept substantially in the starting position by the prestressed springs 91, 92, so that no relative turning between the cup disk 80 and the switching disk 60 takes place. Therefore, a 1:1 transmission occurs from the drive shaft 2 to the driven element in the form of the cup disk 80. The force transmission takes place by way of the inner clamping rollers 22 positioned on the inner side of the frame 24, which are pressed against the drive rotating drive shaft 2. The rapid rotation allows a quick open or closing movement to be made.

As can be seen in FIG. 1, the four inner clamping rollers 22 are formed within the frame 24. Depending on the direction of rotation, two inner clamping rollers 22, which lie diagonally opposite one another, are in force transmission engagement so that a symmetrical torque transmission can take place. Due to this symmetrical arrangement, the clutch module 1 can be operated both clockwise and counterclockwise, so that, in the speed mode, the corresponding movement can be performed independently of the direction of rotation.

If the gripping elements or prosthetic fingers (not represented) come into contact with an object to be gripped, there is a resistance to the rotating movement of the driven element 80. If the resistance does not exceed a limit value, the force transmission remains ensured by the inner clamping rollers 22. If the resistance exceeds a torque that is predetermined by the pre-stressing of the two torsion springs 91, 92, the cup disk 80 and the switching disk 60 turn in relation to each other. This instigates the shift between the speed mode and the force mode, in which the adjustment is slowed down, while the applied torque is increased. This shift takes place in the form of a mechanical sequence control, in which the inner clamping rollers 22 are slowly brought out of contact with the drive shaft 2 independently of the direction of rotation and in a torque-controlled manner. At the same time the outer clamping rollers 21, which in the speed mode do not engage the contact ring 12, are brought into engagement with the contact ring 12 to carry out a torque transmission.

If the resisting torque exceeds the pres-tress of the torsion springs 91, 92, the cup disk 80 and the switching disk 60 turn in relation to each other. The gearwheels 74 cause turning of the switching ring 50 and, in relation thereto, of the gearwheel element 70. As a result, the total of eight switching webs 51, 52, 71 are turned in relation to one another. This turning can be seen well in FIG. 2, which will be further discussed later.

The inner switching webs 51, 71 enter into engagement with the inner clamping rollers 22 and move the latter slightly radially outward within the frame 24, to bring them out of engagement with the drive shaft 2. At the same time, the outer switching webs 52 displace the diagonally opposed outer clamping rollers 21 such that a diagonally opposed pair of clamping rollers 21 enters into engagement with the contact ring 12 in a manner dependent on the direction of rotation.

FIG. 2 shows such a switching position. The inner switching webs 71, 51 have been turned with respect to each other, the switching webs 51 of the switching ring 50 having been turned clockwise, and the switching webs 71 of the gearwheel element 70 having been turned counterclockwise. The outer switching webs 52 of the switching ring 50 have been turned clockwise such that the outer rollers 21 are brought into contact with the contact ring 12. These clamping rollers transmit torques from the clockwise-rotating contact ring 12 by way of the clamping rollers 21 to the frame 24 and from there by way of the switching disk 65 and the cup disk 80 to the force transmission element or unit that is to be driven (not represented). The downwardly bent webs 41 of the spring 40 can be partly seen in FIG. 2.

The clamping rollers 21 that are not involved in the force transmission are brought out of engagement by means of the corresponding switching webs 52 and run in an idling manner. As the torque is reduced based on a reduced opposing force, the relative turning between the switching disk 60 and the cup disk 80 is reversed due to the pre-stressing of the torsion springs 91, 92. The outer switching webs 52 turn counterclockwise, acting by way of the webs 41 to bring the clamping rollers 21 that are initially in contact out of engagement against the action of the spring 40. At the same time, the inner switching webs 71, 51 are turned into their starting position so that the inner clamping rollers 22 can enter into engagement again and bring about a speed mode. Disengagement of the inner clamping rollers 22 when in the force mode requires as little as tenths of a millimeter and is accordingly not represented in FIG. 2.

FIG. 3 shows a section in the plane of the switching ring 50, in which the switching ring 50 has been turned clockwise. The gearwheels 74 are at the respective ends of the partial internal thread 54. The partial external thread 73 has been correspondingly turned counterclockwise. This angular offset leads to the sequence control described above for bringing the clamping rollers 21, 22 into or out of engagement. The angular adjustment between the driven element for the cup disk 80 and the switching disk 60 is performed in a torque-dependent manner. This switching torque can be set by adapting the spring values of the torsion springs 91, 92. The same applies to the response torque, i.e., the beginning of the switching operation.

The engagement of the four outer clamping rollers 21 and the disengagement of the four inner clamping rollers 22 is a smooth transition, so that there is an overdefined force transmission system. At first, the outer clamping rollers 21 are brought into contact slightly with the contact ring 12 while the inner clamping rollers 22 are still in contact with the drive shaft 2. As a result, a gentle shift transfer and a corresponding increase in torque are brought about, so that there is no shift shock or abrupt transition between the two shifting stages.

FIG. 4 shows the clutch module 1 in the fitted state. The clutch module 1 has a very compact construction, since all the components have a small axial extent. The rotationally symmetrical construction of the clutch module makes it possible for it to be used independently of the direction of rotation, so that it is possible for a hand prosthesis to provide both quick opening and quick closing, as well as forceful holding or a high release torque.

The mounting pin 100 facilitates the assembly of the clutch module 1, but may be omitted.

I claim:

1. A clutch module for a prosthesis including a chassis to which at least one finger prosthesis is articulated, the clutch module comprising:
    a drive element;
    a driven element;
    a clutch device;
    first and second clamping bodies, which couple the drive element to the driven element in a torque-controlled manner;
    wherein the clutch device shifts between two gear stages depending on the torques applied to the driven element;
    wherein the clutch device shifts between the gear stages with different increases in speed and independently of the direction of rotation of the drive element;
    wherein the clutch device contacts the first and second clamping bodies.

2. The clutch module of claim 1, wherein the driven element is configured to be driven for a low torque with a high increase in speed and for a high torque with a low increase in speed.

3. The clutch module of claim 1, wherein the clutch device includes two switching elements, which are mounted to be pre-stressed and to turn in relation to each other, wherein the switching elements have switching webs or switching pins, which can be brought into contact with the clamping bodies in a torque-controlled manner.

4. The clutch module of claim 3, wherein the switching elements are kept pre-stressed by springs.

5. The clutch module of claim 1, wherein the drive element is coupled to a gear mechanism which has a contact ring, which contacts the first clamping bodies to transmit high torque.

6. The clutch module of claim 1, wherein the first and second clamping bodies are arranged on a common driver disk.

7. The clutch module of claim 6, wherein the driver disk includes a frame on which the first clamping bodies are arranged to provide a low increase in speed.

8. The clutch module of claim 6, wherein the driver disk includes a frame, in which the second clamping bodies are arranged for a high increase in speed.

9. The clutch module of claim 6, wherein gearwheels, which engage and turn a switching ring in relation to a switching disk and a switching element, are mounted on the driver disk.

10. A clutch module for a prosthesis including a chassis to which at least one finger prosthesis is articulated, the clutch module comprising:
   a drive element;
   a driven element;
   a clutch device;
   wherein the clutch device shifts between two gear stages depending on the torques applied to the driven element;
   wherein the clutch device shifts between the gear stages with different increases in speed and independently of the direction of rotation of the drive element;
   wherein the clutch device includes two switching elements, which are mounted to be pre-stressed and to turn in relation to each other, wherein the switching elements have switching webs or switching pins, which can be bought into contact with the clamping bodies in a torque-controlled manner.

11. The clutch module of claim 10, wherein the clutch device contacts first and second clamping bodies, which couple the drive element to the driven element in a torque-controlled manner.

12. The clutch module of claim 10, wherein the driven element is configured to be driven for a low torque with a high increase in speed and for a high torque with a low increase in speed.

13. The clutch module of claim 10, wherein the switching elements are kept pre-stressed by springs.

14. A clutch module for a prosthesis including a chassis to which at least one finger prosthesis is articulated, the clutch module comprising:
   a drive element;
   a driven element;
   a clutch device;
   wherein the clutch device shifts between two gear stages depending on the torques applied to the driven element;
   wherein the clutch device shifts between the gear stages with different increases in speed and independently of the direction of rotation of the drive element;
   wherein the clutch device contacts first and second clamping bodies, which couple the drive element to the driven element in a torque-controlled manner;
   wherein the drive element is coupled to a gear mechanism which has a contact ring, which contacts the first clamping bodies to transmit high torque.

15. The clutch module of claim 14, wherein the first and second clamping bodies are arranged on a common driver disk.

16. The clutch module of claim 15, wherein the driver disk includes a frame on which the first clamping bodies are arranged to provide a low increase in speed.

17. The clutch module of claim 15, wherein the driver disk includes a frame, in which the second clamping bodies are arranged for a high increase in speed.

18. The clutch module of claim 15, wherein gearwheels, which engage and turn a switching ring in relation to a switching disk and a switching element, are mounted on the driver disk.

* * * * *